(12) United States Patent
Ankenbauer et al.

(10) Patent No.: US 7,122,355 B2
(45) Date of Patent: Oct. 17, 2006

(54) COMPOSITION AND METHOD FOR HOT START NUCLEIC ACID AMPLIFICATION

(75) Inventors: Waltraud Ankenbauer, Penzberg (DE); Dieter Heindl, Tutzing (DE); Frank Laue, Pachl-Fischen (DE); Andreas Huber, Wielenbach-Haunshofen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 345 days.

(21) Appl. No.: 10/192,902

(22) Filed: Jul. 11, 2002

(65) Prior Publication Data

US 2003/0119150 A1 Jun. 26, 2003

(30) Foreign Application Priority Data

Jul. 11, 2001 (EP) .................. 01115788

(51) Int. Cl.
*C12P 19/34* (2006.01)
(52) U.S. Cl. ..................... 435/91.2; 435/91.1
(58) Field of Classification Search .............. 435/91.1, 435/91.2, 810
See application file for complete search history.

(56) References Cited

U.S. PATENT DOCUMENTS

| | | | |
|---|---|---|---|
| 4,889,818 A | 12/1989 | Gelfand et al. ............. 435/194 |
| 5,118,801 A | 6/1992 | Lizardi et al. ............... 536/27 |
| 5,210,015 A | 5/1993 | Gelfand et al. ................ 435/6 |
| 5,322,785 A | 6/1994 | Comb et al. ................ 435/194 |
| 5,352,778 A | 10/1994 | Comb et al. ............... 536/23.2 |
| 5,436,149 A | 7/1995 | Barnes ...................... 435/194 |
| 5,491,086 A | 2/1996 | Gelfand et al. ............. 435/194 |
| 5,545,552 A | 8/1996 | Mathur ..................... 435/252.3 |
| 5,593,840 A * | 1/1997 | Bhatnagar et al. ............. 435/6 |
| 5,629,177 A | 5/1997 | Hyman ....................... 435/91.2 |
| 5,677,152 A | 10/1997 | Birch et al. ................ 435/91.2 |
| 5,693,502 A | 12/1997 | Gold et al. ................ 435/91.2 |
| 5,792,607 A | 8/1998 | Backman et al. ............... 435/6 |
| 5,985,619 A | 11/1999 | Sutherland et al. ........ 435/91.2 |
| 6,174,670 B1 | 1/2001 | Wittwer et al. ................ 435/6 |
| 6,174,998 B1 | 1/2001 | Mühlegger et al. ........... 536/4.1 |
| 6,200,757 B1 * | 3/2001 | Kurn et al. ..................... 435/6 |
| 6,274,353 B1 | 8/2001 | Yang ........................ 435/91.2 |
| 6,482,590 B1 * | 11/2002 | Ullman et al. ................. 435/6 |
| 6,509,157 B1 * | 1/2003 | Martinez ....................... 435/6 |

FOREIGN PATENT DOCUMENTS

| | | |
|---|---|---|
| EP | 0258017 B1 | 3/1988 |
| EP | 0455430 B1 | 11/1991 |
| EP | 0547359 B1 | 6/1993 |
| EP | 0547920 B1 | 6/1993 |
| EP | 0624641 B1 | 11/1994 |
| EP | 0669401 B1 | 8/1995 |
| EP | 0693078 B1 | 1/1996 |
| EP | 0701000 B1 | 3/1996 |
| EP | 0744470 A1 | 11/1996 |
| EP | 0822256 A2 | 2/1998 |
| EP | 1088891 A1 | 4/2001 |
| GB | 2293238 A | 3/1996 |
| WO | WO 92/03556 | 3/1992 |
| WO | WO 92/09689 | 6/1992 |
| WO | WO 95/16028 | 6/1995 |
| WO | WO 96/10640 | 4/1996 |
| WO | WO 96/22389 | 7/1996 |
| WO | WO 96/41014 | 12/1996 |
| WO | WO 97/35988 | 10/1997 |
| WO | WO 97/46706 | 12/1997 |
| WO | WO 98/14590 | 4/1998 |

OTHER PUBLICATIONS

Bernad, Antonio et al., "A Conserved 3'-5' Exonuclease Active Site in Prokaryotic and Eukaryotic DNA Polymerases," Cell, vol. 59,219-228, Oct. 6, 1989.
Bernard, Philip S. et al., "Integrated Amplification and Detection of teh C677T Point Mutation in the Methylenetetrahydrofolate Reductase Gene by Fluorescence Resonance Energy Transfer and Probe Melting Curves," Analytical Biochemistry, 255, 101-107 (1998), Article No. AB972427.
Bessman, Maurice J. et al., "Enzymatic Synthesis of Deoxyribonucleic Acid," J. Biochem. (1957) 171-177.
Bult, Carol J. et al., "Complete Genome Sequence of the Methanogenic Archaeon, Methanococcus jannashii," Science, vol. 273, Aug. 23, 1996, 1058-1073.
Buttin, Gerald et al., "Enzymatic Synthesis of Deoxyribonucleic Acid," The Journal of Biological Chemistry, vol. 211, No. 22, Nov. 25, 1966, pp. 5419-5427.
Cheng, Suzanne et al., "Effective amplification of long targets from cloned inserts and human genomic DNA," Proc. Natl. Acad. Sci. vol. 91, pp. 5695-5699, Jun. 1994.
Chien, Alice et al., "Deoxyribonucleic Acid Polymers from the Extreme Thermophile Thermus aquaticus," Journal of Bacteriology, vol. 127, No. 3, Sep. 1976, pp. 1550-1557.

(Continued)

*Primary Examiner*—Kenneth R. Horlick
(74) *Attorney, Agent, or Firm*—Marilyn L. Amick; Roche Diagnostics Operations, Inc.

(57) ABSTRACT

The present invention is directed to a new composition for performing a nucleic acid amplification reaction comprising (i) a thermostable DNA-Polymerase, (ii) a thermostable 3'-5' Exonuclease, and (iii) at least one primer for nucleic acid amplification with a modified 3' terminal residue which is not elongated by said thermostable DNA-Polymerase as well as methods for performing a PCR reaction using this composition. Furthermore, the method is directed to kits comprising such a composition.

8 Claims, 4 Drawing Sheets

OTHER PUBLICATIONS

Chou, Quin et al., "Prevention of pre_PCR mis-priming and primer dimerization improves low-copy-number amplifications," Nucleic Acids Research, vol. 20, No. 7, 1717-1723.

Cline, Janice et al., "PCR fidelity of Pfu DNA polymerase and other thermostable DNA polymerases," Nucleic Acids Research, 1996, vol. 24, No. 18, pp. 3546-3551.

Diaz, R. S. et al., "Accuracy of replication in the polymerase chain reaction. Comparison between Thermotoga maritima DNA polymerase and Thermus aquaticus DNA polymerase," Brazillian Journal of Medical and Biological Research (1998)31:1239-1242.

Kainz, P. et al., "Short Technical Reports," BioTechniques, vol. 28, No. 2 (2000) pp. 278-282.

Kellogg, D.E. et al., "TaqStart Antibody™: "Hot Start" PCR Facilitated by a Neutralizing Monoclonal Antibody Directed Against Taq DNA Polymerase," BioTechniques, vol. 16, No. 6 (1994) pp. 1134-1137.

Klenk, Hans-Peter et al., "The complete genomesequence of the hyperthermophilic, sulphate-reducing archaeon Archaeglobus flugidus," Nature, vol. 390, Nov. 1997, pp. 364-375.

Lawyer, Frances C. et al.., "Isolation, Characterization, and Expression in Escherichia coli of the DNA Polymerase Gene from Thermus aquaticus," The Journal of Biological Chemistry, vol. 264, No. 11, Apr. 15, 1989, pp. 6427-6437.

Lin, Yun et al., "Inhibition of Multiple Thermostable DNA Polymerases by a Heterodimeric Aptamer," J. Mol. Biol. (1997) 271, 100-111.

Moretti, Tamyra et al., "Enhancement of PCR Amplification Yield and Specifity Using AmpliTaq Gold™ DNA Polymerase," BioTechniques, vol. 25, No. 4 (1998) pp. 716-722.

Nilsson, J. et al., "Heat-Mediated Activation of Affinity-Immobilized Taq DNA Polymerase," BioTechniques, vol. 22, No. 4 (1997) pp. 744-751.

Sambrook, J. et al., Molecular Cloning: A Laboratory Manual, Second Edition, Cold Spring Harbor Laboratory Press, 1999 (Table of Contents only).

Sharkey, David J. et al., "Antibodies as Thermolabile Switches: High Temperature Triggering for the Polymerase Chain Reaction," Bio/Technology, vol. 12, May 1994 pp. 506-509.

Siwek, Brigitte et al., "The relative importance of Escherichia coli exonuclease IIII and endonuclease IV for the hydrolysis of 3'-phosphoglycolate ends in polydeoxynucleotides," Nucleic Acids Research, vol. 16, No. 11, 1988, pp. 5031-5037.

Slupphaug, Geir et al., "Low Incorporation of dUMP by some Thermostable DNA Polymerases May Limit Their Use in PCR Amplifications," Analytical Biochemistry, 211, 164-169 (1993).

Smith, Douglas R. et al., "Complete Genome Sequence of Mehtanobacterium thermoautotrophicum ΔH: Functiona Analysis and Comparative Genomics," Journal of Bacteriology, vol. 179, No. 22, Nov. 1997, p. 7135-7155.

Uemori, Takashi et al., "Organization and nucleotide sequence of the DNA polymerase gene from the archaeon Pyrococcu furiosus," Nucleic Acids Research, 1993, vol. 21, No. 2, pp. 259-265.

* cited by examiner

COMPOSITION AND METHOD FOR HOT START NUCLEIC ACID AMPLIFICATION

The present invention is related to the field of molecular biology, and more particular, to nucleic acid amplification processes. More precisely, the invention enhances the specificity of amplification of DNA by means of inhibition of the formation of unspecific amplification products

PRIOR ART BACKGROUND

In vitro nucleic acid synthesis is routinely performed with DNA polymerases with or without additional polypeptides. DNA polymerases are a family of enzymes involved in DNA replication and repair. Extensive research has been conducted on the isolation of DNA polymerases from mesophilic microorganisms such as E. coli. See, for example, Bessman et al., J. Biol. Chem. 223 (1957) 171–177, and Buttin, G. and Kornberg, A., J Biol Chem 241 (1966) 5419–27.

Research has also been conducted on the isolation and purification of DNA polymerases from thermophiles, such as Thermus aquaticus. Chien, A., et al., J Bacteriol 127 (1976) 1550–7 discloses the isolation and purification of a DNA polymerase with a temperature optimum of 80° C. from Thermus aquaticus YT1 strain. U.S. Pat. No. 4,889,818 discloses a purified thermostable DNA polymerase from T. aquaticus, Taq polymerase, having a molecular weight of about 86,000 to 90,000 daltons. In addition, European Patent Application 0 258 017 discloses Taq polymerase as the preferred enzyme for use in the PCR process.

Research has indicated that while Taq DNA polymerase has a 5'-3' polymerase-dependent exonuclease function, Taq DNA polymerase does not possess a 3'-5' exonuclease function (Lawyer, F. C., et al., J Biol Chem 264 (1989) 6427–37; Bernad, A., et al., Cell 59 (1989) 219–28). The 3'-5' exonuclease activity of DNA polymerases is commonly referred to as "proofreading activity". The 3'-5' exonuclease activity removes bases which are mismatched at the 3' end of a primer-template duplex. The presence of 3'-5' exonuclease activity may be advantageous as it leads to an increase in fidelity of replication of nucleic acid strands and to the elongation of prematurely terminated products. As Taq DNA polymerase is not able to remove mismatched primer ends it is prone to base incorporation errors, making its use in certain applications undesirable. For example, attempting to clone an amplified gene is problematic since any one copy of the gene may contain an error due to a random misincorporation event. Depending on the cycle in which that error occurs (e.g., in an early replication cycle), the entire DNA amplified could contain the erroneously incorporated base, thus, giving rise to a mutated gene product.

There are several thermostable DNA polymerases known in the art which exhibit 3'-5'exonuclease activity, like B-type polymerases from thermophilic Archaebacteria which are used for high fidelity DNA amplification. Thermostable polymerases exhibiting 3'-5'exonuclease activity may be isolated or cloned from Pyrococcus (Purified thermostable Pyrococcus furiosus DNA polymerase, Mathur E., Stratagene, WO 92/09689, U.S. Pat. No. 5,545,552; Purified thermostable DNA polymerase from Pyrococcus species, Comb D. G. et al., New England Biolabs, Inc., EP 0 547 359; Organization and nucleotide sequence of the DNA polymerase gene from the archaeon Pyrococcus furiosus, Uemori, T., et al., Nucleic Acids Res 21 (1993) 259–65), from Pyrodictium spec. (Thermostable nucleic acid polymerase, Gelfand D. H., F. Hoffmann-La Roche AG, EP 0 624 641; Purified thermostable nucleic acid polymerase and DNA coding sequences from Pyrodictium species, Gelfand D. H., Hoffmann-La Roche Inc., U.S. Pat. No. 5,491,086), from Thermococcus (e.g. Thermostable DNA polymerase from Thermococcus spec. TY, Niehaus F., et al. WO 97/35988; Purified Thermocccus barossii DNA polymerase, Luhm R. A., Pharmacia Biotech, Inc., WO 96/22389; DNA polymerase from Thermococcus barossii with intermediate exonuclease activity and better long term stability at high temperature, useful for DNA sequencing, PCR etc., Dhennezel O. B., Pharmacia Biotech Inc., WO 96/22389; A purified thermostable DNA polymerase from Thermococcus litoralis for use in DNA manipulations, Comb D. G., New England Biolabs, Inc., U.S. Pat. No. 5,322,785, EP 0 455 430; Recombinant thermostable DNA polymerase from Archaebacteria, Comb D. G., New England Biolabs, Inc., U.S. Pat. No. 5,352,778, EP 0 547 920, EP 0 701 000; New isolated thermostable DNA polymerase obtained from Thermococcus gorgonarius, Angerer B. et al. Boehringer Mannheim GmbH, WO 98/14590).

Another possibility of conferring PCR in the presence of a proofreading function is the use of a mixture of polymerase enzymes, one polymerase exhibiting such a proofreading activity. (e.g. Thermostable DNA polymerase with enhanced thermostability and enhanced length and efficiency of primer extension, Barnes W. M., U.S. Pat. No. 5,436,149, EP 0 693 078; Novel polymerase compositions and uses thereof, Sorge J. A., Stratagene, WO 95/16028). It is common practice to use a formulation of a thermostable DNA polymerase comprising a majority component of at least one thermostable DNA polymerase which lacks 3'-5' exonuclease activity and a minority component exhibiting 3'-5' exonuclease activity e.g. Taq polymerase and Pfu DNA polymerase. In these mixtures the processivity is conferred by the pol I-type enzyme like Taq polymerase, the proofreading function by the thermostable B-type polymerase like Pfu.

High fidelity DNA synthesis is one desirable parameter in nucleic acid amplification, another important feature is the possibility of decontamination. The polymerase chain reaction can amplify a single molecule over a billionfold. Thus, even minuscule amounts of a contaminant can be amplified and lead to a false positive result. Such contaminants are often poducts from previous PCR amplifications (carry-over contamination). Therefore, researchers have developed methods to avoid such a contamination. The procedure relies on substituting dUTP for TTP during PCR amplification to produce uracil-containing DNA (U-DNA). Treating subsequent PCR reaction mixtures with Uracil-DNA-Glycosylase (UNG) prior to PCR amplification the contaminating nucleic acid is degraded and not suitable for amplification. dUTP can be readily incorporated by poll-type thermostable polymerases but not B-type polymerases (Slupphaug, G., et al., Anal Biochem 211 (1993) 164–9) Low incorporation of dUTP by B-type polymerases limits their use in laboratories where the same type of template is repeatedly analyzed by PCR amplification.

Thermostable DNA polymerases exhibiting 3'-5'exonuclease activity were also isolated from eubacterial strains like Thermotoga (Thermophilic DNA polymerases from Thermotoga neapolitana, Slater M. R. et al. Promega Corporation, WO 96/41014; Cloned DNA polymerases from Thermotoga neapolitana and mutants thereof, Hughes A. J. et al., Life Technologies, Inc. WO 96/10640; Purified thermostable nucleic acid polymerase enzyme from Termotoga maritima, Gelfand D. H. et al., CETUS Corporation, WO 92/03556) These enzymes have a strong 3'-5'exonuclease activity which is able to eliminate misincorporated or mismatched bases. A genetically engineered version of this enzyme is commercially availabile as ULTma, a DNA polymerase which can be used without additional polypeptides for the PCR process. This enzyme is able to remove misincorporated bases, incorporate dUTP, but the fidelity is for unknown reasons not higher than that of Taq polymerase (Accuracy of replication in the polymerase chain reaction. Diaz, R. S. and Sabino, E. C., Braz J Med Biol Res 31 (1998) 1239–42; PCR fidelity of Pfu DNA polymerase and other thermostable DNA polymerases, Cline, J., et al., Nucleic Acids Res 24 (1996) 3546–51).

There also exists a high fidelity PCR system which is preferably concomitantly able to incorporate dUTP. According to EP-A-1088891, a thermostable enzyme exhibiting 3'-exonuclease-activity but essentially no DNA polymerase activity may be used, which enhances fidelity of an amplification process when added to a second enzyme exhibiting polymerase activity. Thus, the enzyme can excise mismatched primer ends to allow the second enzyme exhibiting polymerase activity as e.g. Taq polymerase to reassociate and to reassume elongation during a process of synthezising DNA. The enzyme needs also to be able to cooperate as proofreading enzyme with a second enzyme exhibiting polymerase activity. Especially suited for this task is e.g. a thermostable exonuclease III. Preferred is an exonuclease III working from the 3' to 5' direction, cleaving 5' of the phosphate leaving 3' hydroxyl groups and ideally working on double stranded DNA only.

Of course, it is advantageous, if the enzyme is active at 70° C. to 80° C., stable enough to survive the denaturation cycles and inactive at lower temperatures to leave the PCR products undegraded after completion of the PCR process. Enzymes exhibiting these features can be derived from thermophilic eubacteria or related enzymes from thermophilic archaea. Genomes of three thermostable archaebacteria are sequenced, *Methanococcus jannaschii* (Complete Genome Sequence of the Methanogenic Archaeon, *Methanococcus jannaschii*, Bult, C. J., et al., Science 273 (1996) 1058–73), *Methanobacterium thermoautotrophicum* (Complete genomic sequence of *Methanobacterium thermoautotrophicum* H: Functional Analysis and Comparative Genomics, Smith, D. R., et al., J Bacteriol 179 (1997) 7135–55) and *Archaeoglobus fulgidus* (The complete genome sequence of the hyperthermophilic, sulfate-reducing archaeon *Archaeoglobus fulgidus*, Klenk, H. P., et al., Nature 390 (1997) 364–70).

In particular, EP-A-1088891 discloses a thermostable enzyme obtainable from *Archaeoglobus fulgidus*, which catalyzes the degradation of mismatched ends of primers or polynucleotides in the 3' to 5' direction in double stranded DNA. The gene encoding the thermostable exonuclease III obtainable from *Archaeoglobus fulgidus* (Afu) was cloned, expressed in *E. coli* and isolated. The enzyme is active under the incubation and temperature conditions used in PCR reactions. The enzyme supports DNA polymerases like Taq in performing DNA synthesis at low error rates and synthesis of products of more than 3 kb on genomic DNA—the upper range of products synthesized by Taq polymerase—in good yields with or without dUTP present in the reaction mixture. Preferably, 50–500 ng of the exonuclease III obtainable from Afu were used per 2.5 U of Taq polymerase in order to have an optimal PCR performance. More preferably is the use of 67 ng to 380 ng of the exonuclease III obtainable from Afu per 2.5 U of the Taq polymerase in the PCR reaction.

Another major problem with nucleic acid amplification and more especially with PCR is the generation of unspecific amplification products. In many cases, this is due to an unspecific oligonucleotide priming and subsequent primer extension event prior to the actual thermocycling procedure itself, since thermostable DNA polymerases are also moderately active at ambient temperature. For example, amplification products due to eventually by chance occuring primer dimerisation and subsequent extension are observed frequently. In order to overcome this problem, it is well known in the art to perform a so called "hot start" PCR, wherein one component essential for the amplification reaction is either separated from the reaction mixture or kept in an inactive state until the temperature of the reaction mixture is being raised for the first time. Since the polymerase cannot function under these conditions, there is no primer elongation during the period when the primers can bind non specifically. In order to achieve this effect, several methods have been applied:

a) Physical Separation of the DNA Polymerase

The physical separation can be obtained for example by a barrier of solid wax, which separates the compartment containing the DNA polymerase from the compartment containing the bulk of the other reagents. During the first heating step the wax is then melting automatically and the fluid compartments are mixed (Chou, Q., et al., Nucleic Acids Res 20 (1992) 1717–23). Alternatively, the DNA polymerase is affinity immobilized on a solid support prior to the amplification reaction and only released into the reaction mixture by a heat mediated release (Nilsson, J., et al., Biotechniques 22 (1997) 744–51). Both methods, however are time consuming and unconvenient to perform.

b) Chemical Modification of DNA Polymerase

For this type of hot start PCR, the DNA polymerase is reversibly inactivated as a result of a chemical modification. More precisely, heat labile blocking groups are introduced into the Taq DNA polymerase which render the enzyme inactive at room temperature. These blocking groups are removed at high temperature during a pre-PCR step such that the enzyme is becoming activated. Such a heat labile modification, for example can be obtained by coupling Citraconic Anhydride or Aconitric Anhydride to the Lysine residues of the enzyme (U.S. Pat. No. 5,677,152). Enzymes carrying such modifications are meanwhile commercially availabile as Amplitaq Gold (Moretti, T., et al., Biotechniques 25 (1998) 716–22) or FastStart DNA polymerase (Roche Molecular Biochemicals). However, the introduction of blocking groups is a chemical reaction which arbitrarily occurs on all sterically available Lysine residues of the enzyme. Therefore, the reproducibility and quality of chemically modified enzyme preparations may vary and can hardly be controlled.

c) DNA Polymerase Inhibition by Nucleic Acid Additives

Extension of non-specifically annealed primers has been shown to be inhibited by the addition of short doublestranded DNA fragments (Kainz, P., et al., Biotechniques 28 (2000) 278–82). In this case, primer extension is inhibited at temperatures below the melting point of the short double stranded DNA fragment, but independent from the sequence of the competitor DNA itself. However, it is not known, to which extent the excess of competitor DNA influences the yield of the nucleic acid amplification reaction.

Alternatively, oligonucleotide Aptamers with a specific sequence resulting in a defined secondary structure may be used. Such Aptamers have been selected using the SELEX Technology for a very high affinity to the DNA polymerase (U.S. Pat. No. 5,693,502), (Lin, Y. and Jayasena, S. D., J Mol Biol 271 (1997) 100–11). The presence of such Aptamers within the amplification mixture prior to the actual thermocycling process itself again results in a high affinity binding to the DNA polymerase and consequently a heat labile inhibition of its activity. Due to the selection process, however, all so far available Aptamers can only be used in combination with one particular species of DNA polymerase.

d) Taq DNA Antibodies

An alternative approach to achieve heat labile inhibition of Taq DNA polymerase is the addition of monoclonal antibodies raised against the purified enzyme (Kellogg, D. E., et al., Biotechniques 16 (1994) 1134–7; Sharkey, D. J., et al., Biotechnology (N Y) 12 (1994) 506–9). Like the oligonucleotide Aptamers, the antibody binds to Taq DNA polymerase with high affinity at ambient temperatures in an inhibitory manner. The complex is resolved in a preheating step prior to the thermocycling process itself. This leads to a substantial time consuming prolongation of the amplification as a whole, especially if protocols for rapid thermocycling are applied (WO 97/46706).

U.S. Pat. No. 5,985,619 discloses a specific embodiment for performing PCR using a hot start antibody, wherein besides Taq polymerase, e.g. Exonuclease III from *E. coli* is added as a supplement to the amplification mixture in order to digest unspecific primer dimer intermediates. As disclosed above, Exonuclease III recognizes doublestranded DNA as a substrate, like, for example, target/primer- or target/primer extension product hybrids. Digestion is taking place by means of cleavage of the phosphodiester bond at the 5' end of the 3' terminal deoxynucleotide residue. Since this type of exonuclease is active at ambient temperatures, all unspecifically annealed primers and primer extension products therefore are digested. This results in some embodiments in an even enhanced specifity of the amplification reaction. Yet, digestion of the unspecific primers dependent on the duration of the preincubation time may lead to a substantial and uncontrolled decrease in primer concentration, which in turn may affect the amplification reaction itself.

e) Usage of Exonucleases

Another alternative for increasing amplification efficiency is the use of phosphorothioate oligonucleotide primers in combination with an exonuclease III in the PCR reaction mixes (EP 0 744 470). In this case, a 3' exonuclease, which usually accepts double stranded as well as single stranded DNA substrates, degrades duplex artefacts such as primer dimers as well as carry over amplicons, while leaving the single stranded amplification primers undegraded. Similariliy, the usage of primers with abasic modified 3' ends and template dependent removal by *E. coli* Endonuclease IV has been suggested (U.S. Pat. No. 5,792,607). However, there exist several major draw backs of this methods:

First, oligonucleotides containing phosphorothioate residues can not be synthesized in a stereoisomerically pure manner. Moreover, their hybridisation temperatures are different as compared to unmodified oligonucleotides of the same sequence and unspecific hybridization events are observed frequently.

Second, primers containing phosphorothioate residues even at their 3' ends can still be elongated by the DNA polymerase, which is already present in the reaction mixture.

In other words, the effect of the exonuclease is at least partially compensated by the presence of the polymerase itself.

Third, the enzymatic acitivity of *E. coli* Endonuclease IV is very low in the presence of Mg++ ions (Siwek, B., et al., Nucleic Acids Res 16 (1988) 5031–8). Yet, dependent on the specific type of assay, an exact significant Mg++ concentration is an essentiall prerequisite for a successful PCR amplification reaction, which renders application of an endonuclease IV in a PCR sample quite ineffective.

Fourth and most important, conventional nucleases like *E. coli* Exonuclease III or *E. coli* Endonuclease IV are thermolabile and therefore only active prior to the thermocycling procedure itself. As a consequence, unspecific primer binding and extension is only inhibited prior but not during the temperature cycling process.

In view of the outlined prior art it was an object of the invention to provide an alternative composition and method for hot start PCR, which allows for an inhibition of unspecific priming and primer extension not only prior to the amplification process itself but also during the thermocycling process. More precisely, it was an object of the invention to provide an alternative composition and method for hot start PCR, where no extension of unspecifically annealed primers can take place.

BRIEF DESCRIPTIONS OF THE INVENTION

The new invention provides a composition for performing a nucleic acid amplification reaction comprising
   a thermostable DNA-Polymerase,
   a thermostable 3'-5' Exonuclease, and
   at least one primer for nucleic acid amplification with a modified 3' terminal residue which is not elongated by said thermostable DNA-Polymerase.

Preferably, the thermostable 3'-5' Exonuclease is more active at temperatures between 37° C. and 72° C. and less active at temperatures below 37° C. The thermostable Exonuclease may either be an Exonuclease III homologue or a mutated DNA-Polymerase with no or reduced Polymerase activity.

In a specific embodiment which is useful for Real Time PCR analysis, the composition may further comprise a compound for the detection of the amplification product.

With respect to the amplification primers it is preferable, if at least one primer is modified at the 3' end by a phosphate group or by a chemical moiety which is linked to the 3' terminal deoxynucleotide via a phosphate group. Alternatively, the 3' terminal residue is a Dideoxynucleotide or any other modified nucleotide or nucleotide analog which can not be elongated by a DNA polymerase. In another embodiment, the 3' terminal nucleotide may be replaced by a non nucleoside modifier or an abasic site.

The new invention is also directed to kits comprising a composition as disclosed above or kits which comprise separate storage vessels for a thermostable DNA-Polymerase, a thermostable 3'-5' Exonuclease, and at least one primer for nucleic acid amplification with a modified 3' terminal residue which is not elongated by said thermostable DNA-Polymerase.

In another aspect, the invention is directed to a method for performing an amplification of a template nucleic acid, comprising
   a) providing a reaction mixture comprising at least one primer which is modified at its 3' terminal residue such that said primer is not elongated by a thermostable DNA-Polymerase b) removing said modification without addition of further reaction mixture components by raising the temperature of said reaction mixture c) amplification of the template nucleic acid Preferably, the 3' terminal residue of at least one primer is removed by a thermostable exonuclease. Most preferably, such a method according to the invention may be carried out using a composition as disclosed above.

DETAILED DESCRIPTION

The new invention provides a new concept of hot start PCR in order to overcome the problems of all hot start methods known in the art. It is primarily based on the possibility to prevent primer elogation at low temperatures by introducing chemical modifications at the 3' end of at least one primer. In order to make the primer accessible at typical PCR elongation temperatures, the concept includes the use of a thermostable exonuclease which is inactive at ambient temperatures or below thus leaving the modified primer at these temperatures unaffected. Upon temperature increase, the exonuclease becomes active and capable of removing the 3' modification of the primer thus enabeling the primer to participate in the amplification reaction itself.

Preferably, this exonuclease activity is a 3'-5' exonuclease which especially recognizes such template-primer hybrids as substrates. This is the case for E. coli exonuclease III and homologues from other organisms, which recognize double stranded DNA with a 5' overhang as a preferred substrate and are especially capable of digesting the recessed 3' end of the substrate in 3'-5' direction.

In a first aspect, the new invention provides a composition for performing a nucleic acid amplification reaction comprising a) a thermostable DNA-Polymerase, b) a thermostable 3'-5' Exonuclease, and c) at least one primer for nucleic acid amplification with a modified 3' terminal residue which is not elongated by said thermostable DNA-Polymerase.

The thermostable polymerase as the first component may be any kind of DNA dependent or RNA dependent DNA polymerase, preferably Taq Polymerase from *Thermus aquaticus*. In a specific embodiment, a mixture of thermostable polymerases is used, wherein one polymerase Taq polymerase is providing high processivity and a second enzyme is providing proofreading activity (e.g. ROCHE Molecular Biochemicals, No. 1732641).

The thermostable exonuclease as the second component is preferably an exonuclease III homologue which may be originated from any thermostable organism. In the context of this invention, an exonuclease III homologue is defined as an enzyme which recognizes double stranded DNA with a 5' overhang as a substrate and is capable of removing nucleotide residues from the 3' recesssed end. Furthermore, in the context of this invention, the term "thermostable" is defined as an enzyme which retains more than 50%, preferably more than 80% and most preferably more than 90% of its activity after 60 minutes of incubation at 70° C.

Preferably, the thermostable 3'-5' Exonuclease is more active at temperatures between 37° C. and 72° C. and less active at temperatures below 37° C. In other words, the enzymatic activity of the enzyme at any temperature below 37° C. is in any case lower as compared to the enzymatic activity at any temperature between 37° C. and 72° C. The temperature optimum for the enzyme consequently may be in the range between 50° C. and 85° C.

A thermostable exonuclease III homologue from *Archaeoglobus fulgidus* (Afu ExoIII) has been disclosed recently (EP-A-1088891), which is especially suitable for hot start protocols according to the invention. The advantage of the use of the enzyme in comparison with other enzymes is that the enzyme is clearly preferably active on double stranded DNA, and is highly active at temperatures between 37° C. and 72° C. but has a low activity at temperatures between 20° C. and 37° C.

Alternatively, the thermostable 3'-5' exonuclease may be a mutated DNA polymerase with no or substantially reduced polymerase activity but sufficiently high 3'-exonuclease-activity. Reduced DNA polymerase activity in this context means less than 50% of said activity of an enzyme exhibiting DNA polymerase activity.

The third component of the inventive composition is a primer for nucleic acid amplification with a modified 3' terminal residue which is not elongated by said thermostable DNA-Polymerase. Preferably, both amplification primers are modified in such a way that they are not capable of being elongated by DNA polymerases. As shown in the examples, however, it is also sufficient in case only one primer of a primer pair is modified at its 3' end. For multiplex applications, wherein more than one specific amplification product is generated from one sample in the same reaction vessel the invention requires that at least one primer of each target nucleic acid to be amplified is modified.

It is preferable, if at least one primer is modified at the 3' end by a phosphate group or by a chemical moiety which is linked to the 3' terminal deoxynucleotide via a phosphate group. From the results of using various different 3' terminal modifications it seems reasonable to conclude that thermostable exonuclease III or its homologues are able to cut phosphate group linkages at the 3' terminal end of an oligonucleotide. In this context the chemical moiety linked via the phosphate group to the primer does not substantially affect the efficiency of the reaction.

Alternative to the modification by a phosphate group other chemical moieties which prevent primer extension can be attached to the 3' end of the primer. The chemical moiety can be a nucleoside or a nucleoside analog which prevents elongation by the polymerase. However there is no limitation regarding the 3' blocking entity, since it is only essential that there is a neighbored phosphate group which can be attacked by the Exonuclease III enzyme.

For example, the 3' terminal residue may be a Dideoxynucleotide. In this case, it seems probable that the complete 3' terminal Dideoxynucleotide residue is cut off from the primer by the thermostable exonuclease III homologue. This also seems to take place in a still other embodiment of the invention, wherein the 3' terminal residue itself is modified with a chemical entity not connected to a phosphate group, wherein nevertheless the oligonucleotide can not be elongated by a DNA polymerase reaction.

Other 3' terminal modifications at the phosphate moiety, for example, include but are not limited to alkylspacers, e.g. propylspacers, or 2'tert butyl silyl nucleosides. In addition, the 3' modification can also consist of more than one modifier.

Synthesis of 3' terminal modified oligonucleotide primers can be done by any method known in the art. Phosphate groups, for example, can be introduced by using a special type of commercially available controlled pore glass particle as a starter matrix for oligonucleotide synthesis (Glen Research Cat No. 20-2900-xx) Dideoxynucleotides can preferentially be introduced by an enzymatic reaction using the terminal transferase enzyme or by using commercially available 2' 3' dideoxy CPG (Glen Research Cat No. 20-2017-xx).

In a specific embodiment the inventive composition may be used for Real Time PCR monitoring. For, example, the composition may further comprise one or more compounds in order to detect the amplification product, e.g. one or more labeled nucleic acid hybridization probes, wherein the label e.g. is fluorescent label.

Alternatively, the composition may comprise a fluorescent double strand DNA binding dye. Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SYBR Green I (Molecular Probes), for example, do not affect the efficiency of the PCR reaction.

Regarding the use of fluorescently labeled hybridization probes there exist different possibilities:

First a single-stranded TaqMan hybridization probe may be used, which is labeled with a fluorescent entity, the fluorescence emission of which is quenched by a second label on the same probe which may act as a quenching compound. During the annealing step of the PCR reaction, the probe hybridizes to its target sequence, and, subsequently, during the extension of the primer, the DNA polymerase having a 5'–3'-exonuclease activity digests the hybridization probe into smaller fragments, such that the fluorescent entity is separated from the quencher compound. After appropriate excitation, fluorescence emission can be monitored as an indicator of accumulating amplification product (U.S. Pat. No. 5,210,015).

Second, similar to the Taq Man Probes, a Molecular Beacon oligonucleotide is labeled with a fluorescent compound and a quencher compound, which due to the secondary structure of the molecule are in close vicinity to each other. Upon binding to the target DNA, the intramolecular hydrogen bonding is broken, and the fluorescent compound located at one end of the probe is separated from the quencher compound, which is located at the opposite end of the probe (Lizardi et al., U.S. Pat. No. 5,118,801).

Third, two oligonucleotide hybridization probes each labeled with a fluorescent moiety may be used which are capable of hybridizing to adjacent but non overlapping regions of one strand of the amplification product. Preferably, one oligonucleotide is labeled at the 5' end and the second oligonucleotide is labeled at the 3' end (U.S. Pat. No. 6,174,670). When hybridized to the target DNA, the two fluorescent labels are brought into close contact, such that fluorescence resonance energy transfer between the two fluorescent moieties can take place. As a consequence, the hybridization can be monitored through excitation of the donor moiety and subsequent measurement of fluorescence emission of the second acceptor moiety. In a similar embodiment, only one fluorescently labeled probe is used, which together with one appropriately labeled primer may also serve as a specific FRET pair (Bernard, P. S., et al., Anal Biochem 255 (1998) 101–7).

For real time PCR formates based on the usage of hybridization probe (s), the prescence of a thermostable exonuclease III requires a suitable blocking method for the 3' end of the detection probe(s) in order to avoid 3'digestion. Unlike amplification primers, hybridization probes are not elongated during the PCR reaction such that removal of residues in 3'-5' direction would render the probe inactive.

Different suitable blocking methods have been found: For example, introduction of two 2' methoxy nucleosides at the 3' end of the probe results in exonuclease III resistence of the probe(s). In contrast, additional substitution of two 3' bases by 2' tert butyl silyl nucleosides does not result in increased nuclease resistence. Therefore, it is reasonable that in the case of 2' modifications, increased exonuclease resistance only occurs if the modified nucleotide residues are able to hybridize with the complementary strand. Therefore, all 2' modifications which do not dramatically influence hybridization are suitable for the purpose of this invention.

Of course, probe stabilization is not limited to 2' modifications. Another approach consistent with the invention is to use oligonucleotides or oligonucleotide chimeras with totally or partially modified backbones. The expert skilled in the art will be able to easily choose different modifications which are well known from the antisense technology. For example, backbone modifications like phosphothioates or methylphosphonates also result in increased nuclease resistance.

A still further example is the use of C nucleoside analogs as 3' terminal residues. C-Nucleosides have been disclosed in detail in U.S. Pat. No. 6,174,998.

The new invention is also directed to kits comprising a composition containing
a) a thermostable DNA-Polymerase
b) a thermostable 3'-5' Exonuclease
c) at least one primer for nucleic acid amplification with a modified 3' terminal residue which is not elongated by said thermostable DNA-Polymerase.

Alternatively, a kit according to the invention may comprise separate storage vessels for a thermostable DNA-Polymerase, a thermostable 3'-5' Exonuclease, and at least one primer for nucleic acid amplification with a modified 3' terminal residue which is not elongated by said thermostable DNA-Polymerase. It is also within the scope of the invention, if two of the three components mentioned above are kept within one storage vessel.

In addition, these kits may comprise additional buffers or reagents suitable for nucleic acid amplification reactions such as deoxynucleoside triphosphates. The kits may also contain reagents for detection of the amplification products like double strand DNA binding dyes, e.g. SybrGreenI (molecular probes), or oligonucleotide hybridization probes.

In another aspect, the invention is directed to a method for performing an amplification of a template nucleic acid, comprising
a) providing a reaction mixture comprising at least one primer which is modified at its 3' terminal residue such that said primer is not elongated by a thermostable DNA-Polymerase
b) removing said modification without addition of further reaction mixture components by raising the temperature of said reaction mixture
c) amplification of the template nucleic acid Preferably, the 3' terminal residue of the at least one primer is removed by a thermostable exonuclease. Most preferably, such a method according to the invention may be carried out using a composition according to the invention.

Alternatively, removal of said modification can be thermally induced in case the linker between the 3' terminal residue and the modification is heat labile.

The following examples, references, sequence listing and figures are provided to aid the understanding of the present invention, the true scope of which is set forth in the appended claims. It is understood that modifications can be made in the procedures set forth without departing from the spirit of the invention.

| IV | | |
|---|---|---|
| 1. | Roche MWM/II | |
| 2. | primer not blocked, | 2.5 UTaq |
| 3. | primer not blocked, | 2.5 U Taq and 38 ng Afu-ExoIII |
| 4. | primer not blocked, | 2.5 U Taq and 76 ng Afu-ExoIII |
| 5. | primer not blocked, | 2.5 U Taq and 101 ng Afu-ExoIII |
| 6. | primer not blocked, | 2.5 U Taq and 152 ng Afu-ExoIII |
| 7. | primer blocked, | 2.5 U Taq |
| 8. | primer blocked | 2.5 U Taq and 38 ng Afu-ExoIII |
| 9. | primer blocked | 2.5 U Taq and 76 ng Afu-ExoIII |
| 10. | primer blocked | 2.5 U Taq and 101 ng Afu-ExoIII |
| 11. | primer blocked | 2.5 U Taq and 152 ng Afu-ExoIII |
| 12. | Roche MWM/II | |

Figure 2:
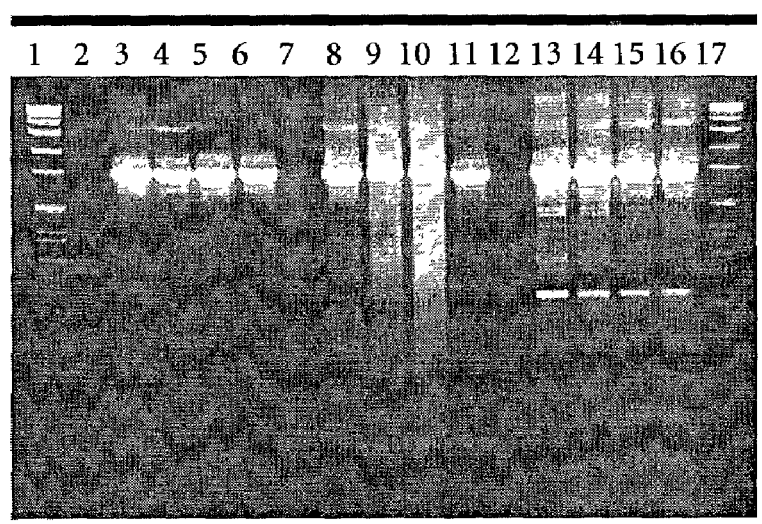

FIG. 2
Exo-Start-PCR induction with 3'-P-blocked primers, Afu-Exonuclease III and thermostable DNA polymerases
1. Roche MWM VII
2. 2.5 U ROCHE Taq
3. 2.5 U ROCHE Taq and 50 ng Afu-ExoIII
4. 2.5 U ROCHE Taq and 33 ng Afu-ExoIII
5. 2.5 U ROCHE Taq and 25 ng Afu-ExoIII
6. 2.5 U ROCHE Taq and 20 ng Afu-ExoIII
7. 1 µl AdvanTaq Taq
8. 1 µl AdvanTaq and 50 ng Afu-ExoIII
9. 1 µl AdvanTaq and 33 ng Afu-ExoIII
10. 1 µl AdvanTaq and 25 ng Afu-ExoIII
11. 1 µl AdvanTaq and 20 ng Afu-ExoIII
12. 0.5 µl Klen Taql
13. 0.5 µl Klen Taql and 50 ng Afu-ExoIII
14. 0.5 µl Klen Taql and 33 ng Afu-ExoIII
15. 0.5 µl Klen Taql and 25 ng Afu-ExoIII
16. 0.5 µl Klen Taql and 20 ng Afu-ExoIII
17. Roche MWM VII FIG. 3
PCR induction with 3'-ddC-blocked primers, Afu-Exonuclease III and Taq DNA polymerase
1. Roche MWM VII
2. 2.5 U ROCHE Taq
3. 2.5 U ROCHE Taq and 100 ng Afu-ExoIII
4. 2.5 U ROCHE Taq and 50 ng Afu-ExoIII
5. 2.5 U ROCHE Taq and 33 ng Afu-ExoIII
6. 2.5 U ROCHE Taq and 25 ng Afu-ExoIII
7. 2.5 U ROCHE Taq and 20 ng Afu-ExoIII
8. 2.6 U ExpandHighFidelity enzyme in ExpandHiFi buffer
9. Roche MWM VII FIG. 4
PCR induction with 3'-Fluorescein-blocked primers and Exonuclease III
Amplifications in lanes 3–7 have been carried out using primers according to Seq. Id. No. 5 (unblocked) and 6 (blocked). Amplifications in lanes 8–12 have been carried out using primers according to Seq. Id. No. 7 (unblocked) and 8 (blocked).
1. Roche MWM VI
2. Roche MWM V
3. 1.6 U Taq
4. 1.6 U Taq and 76 ng Afu-ExoIII
5. 1.6 U Taq and 101 ng Afu-ExoIII
6. 1.6 U Taq and 152 ng Afu-ExoIII
7. control (PCR mix without DNA andAfu-Exo 111)
8. 1.6 U Taq
9. 1.6 U Taq and 76 ng Afu-ExoIII
10. 1.6 U Taq and 101 ng Afu-ExoIII
11. 1.6 U Taq and 152 ng Afu-ExoIII
12. control (PCR mix without DNA and Afu-ExoIII)
13. Roche MWM V
14. Roche MWM VI

EXAMPLE 1

Oligonucleotide Synthesis
For oligonucleotide synthesis, the following reagents were used:
LightCycler Red 640 NHS ester (Roche Molecular Biochemicals cat no. 2015161)
LightCycler Fluorescein CPG (Roche Molecular Biochemicals cat no. 3138178)
3' phosphate CPG (Glen Research Cat No. 20-2900-xx)
C3 propyl spacer (Glen Research Cat No 10-1913-xx-)
2' OMe-G phosphoramidite (Glen Research Cat No 10-3121-xx)
2' OMe-C-phosphoramidite (Glen Research Cat No 10-3110-xx)
2' OMe-U-phosphoramidite (Glen Research Cat No 10-3130-xx)
2' 3' dideoxy C CPG (Glen Research Cat No. 20-2017-xx)
Oligonucletide synthesis was performed according to standard protocols on a DNA synthesis machine (Applied Biosystens model ABI 394-08) Synthesis scale was 1.0 µmol. Solid supports were purchased from GlenResearch in prefilled columns or filled in empty synthesis columns (Glen Research cat no. 20-0030-00) and the columns were adapted to the corresponding synthesizer position. Standard 3' phosphoramidites ([(MeO)2Tr]ib2Gd, [(MeO)2Tr]bz6Ad, [(MeO)2Tr]bz4Cd, [(MeO)2Tr]Td)) were used. The synthesis was performed according to standard protocols for DNA synthesis.

Primers and 3' blocked primers were synthesized in the "Trityl off" modus. Deprotection was done with 25% $NH_3$/$H_2O$ for 8 h at 55° C. Purification on MonoQ (5.0×50 mm column Amersham Pharmacia Biotech) was performed as follows: Buffer A: 10 mM sodiumhydroxid/water B: 1M sodium chloride in 10 mM sodiumhydroxid/Water, flow rate: 1 ml/min in 30 min from 0% B to 100% B.) Desalting was performed by dialysis LC-Red 640 probes were synthesized according to the pack insert instructions provided together with the LightCycler Red 640 NHS ester. Fluorescein probes were synthesized according to the pack insert instructions provided together with the LightCycler fluorescein CPG.

EXAMPLE 2

Exo-Start-PCR Induction with 3'-P-blocked Primers, Afu-Exonuclease III and Taq DNA Polymerase
PCR was performed to amplify a 2763 bp fragment from the human p53 gene using either unmodified primers according to Seq. Id. No. 1 and 2 or 3'-Phosphate-blocked primers according to Seq.Id. No. 1 and 2. Introduction of the Phosphate modification was achieved as known in the art according to example 1. PCR reactions were set up with 2.5

Units Taq DNA Polymerase (ROCHE Molecular Biochemicals, No. 1435094), without and with addition of 38 to 152 ng A. fulgidus exodeoxyribonuclease III (EP-A-1088891) 200 ng of human genomicDNA (ROCHE Molecular Biochemicals, No. 1691112), 0.4 µM each of the above mentioned primers, 200 µM dNTP's (ROCHE Molecular Biochemicals, No.1969064), 1.5 mM MgCl$_2$, 50 mM Tris-HCl, pH 8,9 (25° C.) and 22 mM (NH$_4$)$_2$SO$_4$a 50 µl final reaction volume.

PCR amplifications were performed under standard conditions:

94° C. for 2 min. (1 cycle)

94° C. for 10 sec.
55° C. for 30 sec. } (35 cycles)
72° C. for 4 min

72° C. for 7 min. (1 cycle)

As a control, PCR was performed with the same but unblocked primers described above. All reactions were performed in Perkin Elmer Block Cycler 9600. After completion of the thermocycling protocol, the mixtures were stopped with 10 µl stop solution and 25 µl of each mixture were separated on a 1% agarose gel.

Figure 1:
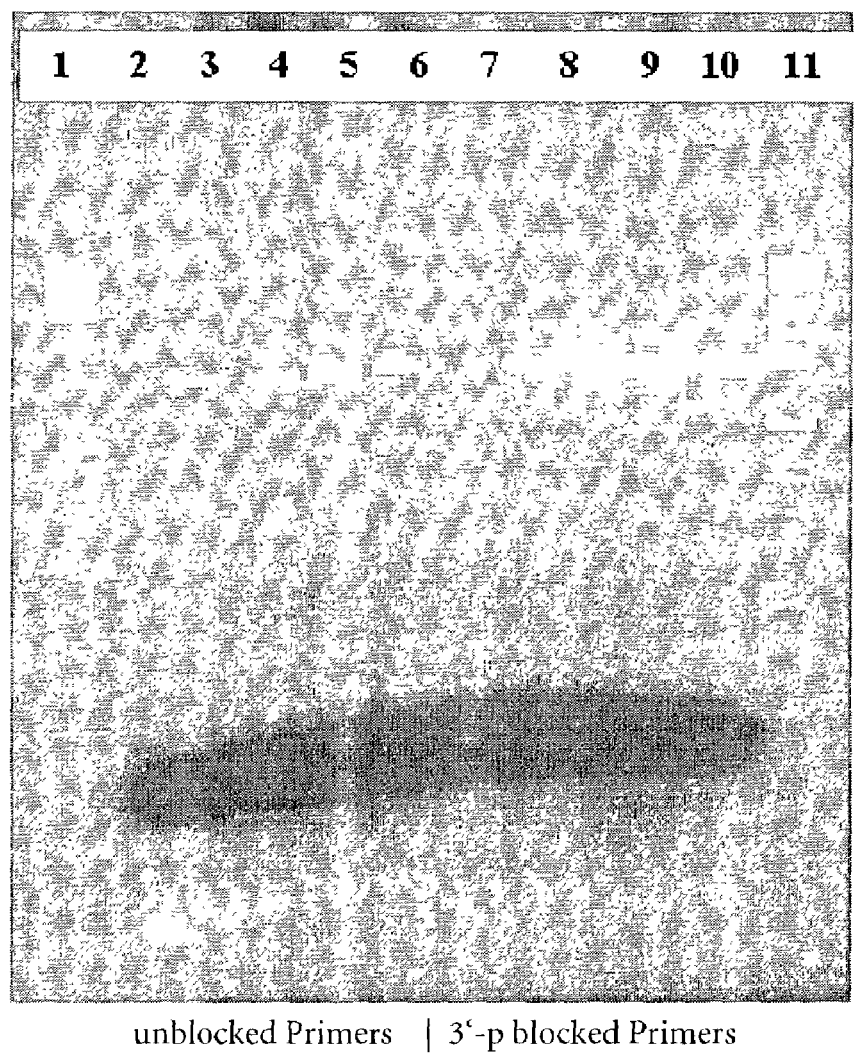
FIG. 1
Exo-Start-PCR induction with 3'-P-blocked primers, Afu-Exonuclease III and Taq DNA polymerase

As shown in FIG. 1, in the absence of Afu ExoIII no PCR product is detectable (lanes 2, 7) in the presence of Afu ExoIII a specific PCR product is obtained (lanes 3–6, 8–11). Moreover, usage of 3' blocked primers according to the invention results in a substantial increase of product yield (compare lanes 8–11 to lanes 3–6) and a desired loss of primer dimers.

EXAMPLE 3

Replacement of Taq Polymerase by Other Type I Polymerases in the ExoIII Induction Step PCR PCR was performed with the same primers blocked at the 3' end with a phosphate group and final concentrations as described in example 1. ROCHE Taq polymerase in this experiment was compared with AdvanTaq™ (Clontech, No. 8432-1) an N-terminal deletion mutant of Taq polymerase and KlenTaq1™ (Ab Peptides, Inc., No. 1001) another N-terminal deletion mutant of Taq polymerase. The PCR mixture components for ROCHE Taq were as described in example 1. Reaction with the other two polymerases were set up with the special shipped reaction buffers and the recommended enzyme volumes without and with addition of 20 to 50 ng A. fulgidus exodeoxyribonuclease III.

PCR amplifications (50 µl) were performed under standard conditions:

94° C. for 2 min. (1 cycle)

94° C. for 10 sec.
55° C. for 30 sec. } (35 cycles)
68° C. for 4 min.

68° C. for 7 min. (1 cycle)

All reactions were performed in Perkin Elmer Block Cycler 9600. After completion of the thermocycling protocol, the mixtures were stopped with 10 µl stop solution and 25 µl of each mixture were separated on a 1% agarose gel.

As shown in FIG. 2 the use of blocked primers in combination with A. fulgidus exodeoxyribonuclease III is applicable to all types of PCR reactions using different types of Taq polymerases.

EXAMPLE 4

PCR Induction with 3'-ddC-Blocked Primers, Afu-Exonuclease III and Taq DNA Polymerase PCR was performed to amplify a 2767 bp fragment from the human p53 gene using primers according to Seq.Id. No. 3 and 4. The oligonucleotides of Seq.Id. Nos. 3 and 4 were chemically blocked by adding one additional ddCMP as described in detailed description and example 1.

PCR reactions were set up with 2.5 Units Taq DNA Polymerase (ROCHE Molecular Biochemicals, No. 1435094), without and with addition of 20 to 100 ng A. fulgidus exodeoxyribonuclease III (EP-A-1088891). The reaction mixture contained in addition: 100 ng of human genomic DNA (ROCHE Molecular Biochemicals, No. 1691112), 0.4 µM each of the above primers, 200 µM each dNTP's (ROCHE Molecular Biochemicals, No. 1969064); 1.25 mM MgCl$_2$, 10 mM Tris-HCl, pH 8.5 (25° C.), 17.5 mM (NH$_4$)$_2$SO$_4$2.5% (v/v) Tween 20 and 1.5% (v/v) DMSO.

PCR amplifications (50 µl) were performed under standard conditions: e.g.

94° C. for 2 min. (1 cycle)

94° C. for 10 sec.
62° C. for 30 sec. } (35 cycles)
68° C. for 4 min.

68° C. for 7 min. (1 cycle)

Also in this experiment, Expand High Fidelity-Polymerase (ROCHE Molecular Biochemicals, No. 1732641) comprising a Taq DNA Polymerase in combination with a 3'-5' nuclease activity from the B type polymerase of Pyrococcus woesii was checked for its ability to remove the ddC-blocked primers prior to the amplification reaction. All reactions were performed in Perkin Elmer Block Cycler 9600. After completion of the thermocycling protocol, 10 µl stop solution were added and 25 µl of each mixture were separated on a 1% Agarose gel.

Figure 3:
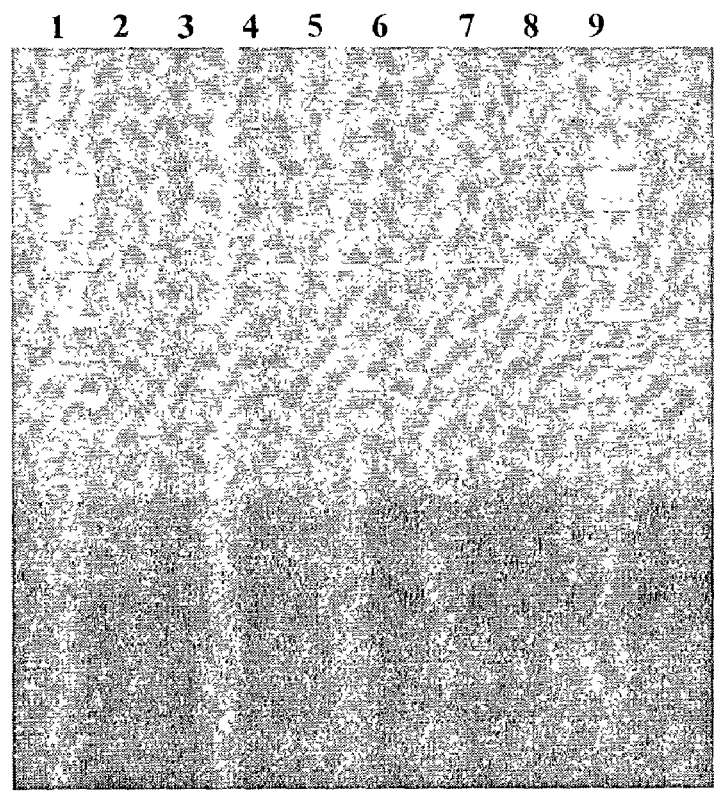

The results as shown in FIG. 3 demonstrate that Taq polymerase alone was not able to remove the blocked base of the primers and start elongation (lane 2). Similarly, the exonuclease of the HighFidelity System was not capable to catalyze this removal (lane 8). In contrast, balanced mixes of Taq Polymerase and Afu ExoIII nuclease result in an amplification (lanes 4–7). It can be concluded that in case a thermostable polymerase with an additional exonuclease III activity shall be used instead of an enzyme only processing exonuclease III activity, it is necessary to use said thermostable enzyme in such a way that its polymerase activity is lost or at least significantly reduced.

EXAMPLE 5

PCR with 3'-Fluorescein-blocked Primers and Exonuclease III

PCR was performed with primers amplifying a fragment of the human ApoE gene according to Seq. Id No. 5 and 6, wherein the primer according to Seq. Id. No. 6 was labeled at its 3' end with a Fluorescein moiety according to standard protocols as disclosed in example 1. The size of the PCR fragment is 96 bp. Alternatively, amplification of the same target gene was performed with primers according to Seq. Id. No. 7 and 8, wherein the primer according to Seq. Id. No. 8 was labeled at its 3' end with a Fluorescein moiety according to standard protocols as disclosed in example 1 The size of the PCR fragment is 109 bp.

In both cases PCR reactions were set up with 2 µl LightCycler-DNA Master SYBR GreenI (ROCHE Molecular Biochemicals, No. 2015099), 4 mM $MgCl_2$, 0.5 µM primer each, 10% DMSO, 200 ng of human genomic DNA (ROCHE Molecular Biochemicals, No. 1691112) without and with addition of 76 to 152 ng of *A. fulgidus* exodeoxyribonuclease III. The final reaction volume of 20 µl was adjusted with destined water.

PCR conditions were as follows:

| 1 Cycle: | | |
|---|---|---|
| Denaturation: | 95° C. | 2 min |
| 45 Cycles: | | |
| Denaturation: | 95° C. | 0 s |
| Annealing | 60° C. | 10 s |
| Elongation | 72° C. | 10 s |

Figure 4:
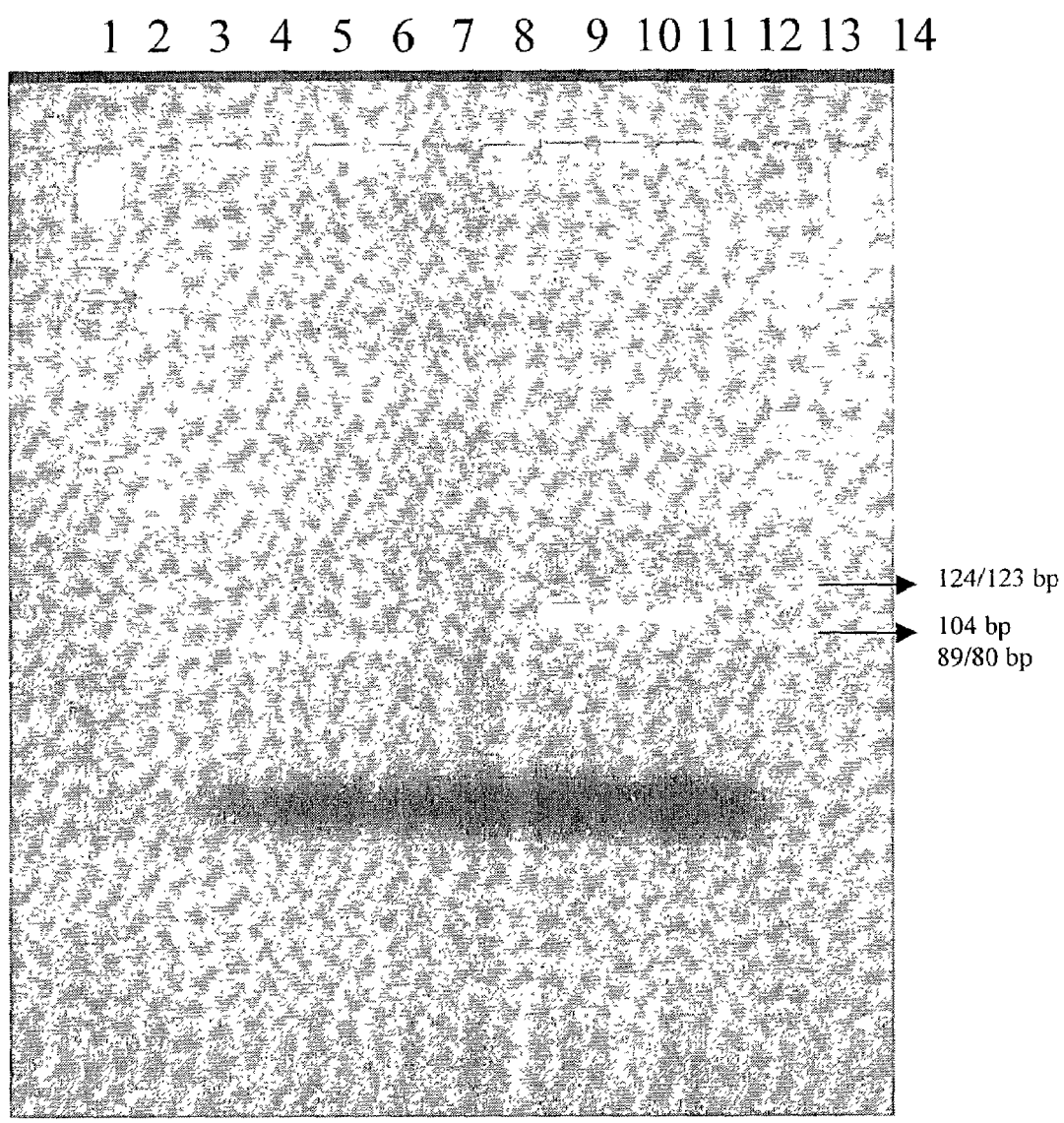

All reactions were performed on a LightCycler (Roche Molecular Biochemicals No. 2011468) which was programmed according to the instructions of the manufacturer's USER manual. After completion of the amplification reaction, 5 µl stop solution were added to the PCR mixture and the mixture was analyzed on a 3% MS agarose gel (ROCHE Molecular Biochemicals, No. 1816586) as shown in FIG. 4.

With the primer pairs used, no amplification products were obtained in the absence of exonuclease III (lanes 3, 8) whereas amplification products were generated in presence of Afu-ExoIII (lanes 4–6, 9–11), indicating that the *Archaeoglogus fulgidus* exonuclease III was able to remove the Fluorescein moiety from the 3' terminus of different primers thus allowing the PCR reactions to take place.

EXAMPLE 6

Temperature Dependence of Afu-Exo III

In six parallel assays, 2 µl Afu ExoIII (0.5 mg/ml) were added to 100 µl reaction mixtures which contained 1 µg of Bam-H1 linearized plasmid pBR 322 in an Expand HiFi buffer (Roche Molecular Biochemials). Samples were incubated for 60 minutes at 20° C., 37° C., 50° C., 60° C., 70° C. and 80° C., respectively. Subsequently, 5 µl of stop solution were added to the incubation mixture and the mixture was then analyzed on a 1% agarose gel. No degradation could be observed in case of incubation at 20° C. and 37° C. Partial degradation of the plasmid was observed in case of incubation at 50° C. or 60° C. Complete degradation of the plasmid was observed in case of incubation at 70° C. and 80° C. indicating, that Afu ExoIII is a thermostable enzyme and has a temperature optimum far above 37° C.

EXAMPLE 7

Real Time PCR with Afu-Exo III using Hybridisation Probe Detection

For detection and quantification of PCR amplicons in Real Time PCR it is essential that colour labeled and blocked hybridisation probes will remain intact during PCR, i.e. Exonuclease III should not be able to cut the blocked/labeled 3'-ends of the probes. For this purpose hybridisation probes with additional modifications at the 3'-end became designed and synthesized according to methods known in the art as disclosed in example 1.

Primers according to SEQ. ID. NO: 9 and 10 in order to amplify a fragment from the β-actin gene were used. FRET-Hybridisation probes were also prepared according to example 1. As acceptor probe, a 5' LCRed-640 labeled oligonucleotide according to SEQ. ID. NO: 11 was prepared, wherein the two 3' terminal nucleosides were 2' methoxy nucleosides. In addition, the last 3' terminal rasidue carried a propylspacer at its 3' end. As a donor probe, a 3' Fluorescein labeled oligonucleotide according to SEQ. ID. NO: 12 was used, wherein the two 3' terminal residues were 2'-methoxy nucleoside residues.

PCR reactions were set up with 2 µl LightCycler-10x DNA Master HybridisationProbe (ROCHE Molecular Biochemicals, No. 20150102), 3 mM $MgCl_2$, 0.5 µM primer each, 0.2 µM probe each, 200 ng human genomic DNA (ROCHE Molecular Biochemicals, No. 1691112) without and with addition of 50 ng *A. fulgidus* exodeoxyribonuclease III. The final reaction volume of 20 µl was adjusted with destiled water. All reactions were performed on a LightCycler (Roche Diagnostics No. 2011468) programmed according to the instructions of the manufacturer's USER manual.

PCR conditions were as follows:

| 1 Cycle: | | |
|---|---|---|
| Denaturation: | 95° C., | 2 min |
| 45 Cycles: | | |
| Denaturation: | 95° C., | 0 s |
| Annealing | 60° C. | 10 s |
| Elongation | 72° C. | 10 s |

Identity of the correct amplicon was detected by melting curve analysis:

| Denaturation: | 95° C. | 30 s |
|---|---|---|
| Annealing: | 50° C. | 15 s |
| Heating: | 95° C. | 0 s |
| cool | 40° C. | 30 s |

The data analysis showed the possibility of DNA amplification, detection and quantification with appropriately modified hybridization probes in presence of exonuclease III.

LIST OF REFERENCES

Bernad, A., et al., Cell 59 (1989) 219–28
Bernard, P. S., et al., Anal Biochem 255 (1998) 101–7
Bessman et al., J. Biol. Chem. 223 (1957) 171–177
Bult, C. J., et al., Science 273 (1996) 1058–73
Buttin, G. and Kornberg, A., J Biol Chem 241 (1966) 5419–27
Chien, A., et al., J Bacteriol 127 (1976) 1550–7
Chou, Q., et al., Nucleic Acids Res 20 (1992) 1717–23
Cline, J., et al., Nucleic Acids Res 24 (1996) 3546–51
Diaz, R. S. and Sabino, E. C., Braz J Med Biol Res 31 (1998) 1239–42
Kainz, P., et al., Biotechniques 28 (2000) 278–82
Kellogg, D. E., et al., Biotechniques 16 (1994) 1134–7
Klenk, H. P., et al., Nature 390 (1997) 364–70
Lawyer, F. C., et al., J Biol Chem 264 (1989) 6427–37
Lin, Y. and Jayasena, S. D., J Mol Biol 271 (1997) 100–11
Moretti, T., et al., Biotechniques 25 (1998) 716–22
Nilsson, J., et al., Biotechniques 22 (1997) 744–51
Sharkey, D. J., et al., Biotechnology (N Y) 12 (1994) 506–9
Siwek, B., et al., Nucleic Acids Res 16 (1988) 5031–8
Slupphaug, G., et al., Anal Biochem 211 (1993) 164–9
Smith, D. R., et al., J Bacteriol 179 (1997) 7135–55
Uemori, T., et al., Nucleic Acids Res 21 (1993) 259–65
EP 0 258 017
EP 0 455 430
EP 0 547 359
EP 0 547 920
EP 0 693 078
EP 0 701000
EP 0 744 470
EP-A-1088891
U.S. Pat. No. 4,889,818
U.S. Pat. No. 5,118,801
U.S. Pat. No. 5,210,015
U.S. Pat. No. 5,322,785
U.S. Pat. No. 5,352,778
U.S. Pat. No. 5,436,149
U.S. Pat. No. 5,491,086
U.S. Pat. No. 5,545,552
U.S. Pat. No. 5,677,152
U.S. Pat. No. 5,693,502
U.S. Pat. No. 5,792,607
U.S. Pat. No. 5,985,619
U.S. Pat. No. 6,174,670
U.S. Pat. No. 6,174,998
WO 92/03556
WO 92/09689
WO 95/16028
WO 96/10640
WO 96/22389
WO 96/41014
WO 97/35988
WO 97/46706
WO 98/14590

The invention claimed is:

1. A composition for nucleic acid amplification comprising:
   a. a thermostable DNA polymerase,
   b. a thermostable 3'-5' exonuclease specific for double stranded DNA with a 5' overhang and having no or reduced polymerase activity, and
   c. at least one primer for nucleic acid amplification with a modified 3' terminal residue which is not elongated by said thermostable DNA polymerase.

2. The composition of claim 1 wherein said is more active at temperatures between 37° C. and 72° C. and less active at temperatures below 37° C.

3. The composition of claim 1 wherein said thermostable exonuclease is either an exonuclease III homologue or a mutated DNA polymerase with no or reduced polymerase activity.

4. The composition of claim 1 further comprising a compound for detection of an amplification product.

5. The composition of claim 1 wherein at least one primer is modified at the 3' end by a phosphate group or by a chemical moiety which is linked to the 3' terminal deoxynucleotide via a phosphate group.

6. The composition of claim 1 wherein at least one primer has a 3' terminal dideoxynucleotide residue.

7. A kit comprising a thermostable DNA polymerase, a thermostable 3'-5' exonuclease specific for double stranded DNA with a 5' overhang and having no or reduced polymerase activity, and at least one primer for nucleic acid amplification with a modified 3' terminal residue which is not elongated by said thermostable DNA polymerase.

8. A method for amplifying a template nucleic acid comprising:
   a. providing a reaction mixture comprising a thermostable DNA polymerase, a thermostable 3'-5' exonuclease specific for double stranded DNA with a 5' overhang and having no or reduced polymerase activity, and at least one primer which is modified at its 3' terminal residue such that said primer is not elongated by the thermostable DNA polymerase and wherein the 3' terminal residue of the primer is removed by the thermostable exonuclease,
   b. removing said modification without addition of further reaction mixture components by raising the temperature of said reaction mixture, and
   c. amplifying the template nucleic acid.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:primer 1

<400> SEQUENCE: 1
gtcccaagca atggatgat                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:primer 2

<400> SEQUENCE: 2
tggaaacttt ccacttgat                                                    19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:primer 3

<400> SEQUENCE: 3
caagcaatgg atgatttgat g                                                 21

<210> SEQ ID NO 4
<211> LENGTH: 21
```

```
<212> TYPE: DNA
<213> ORGANISM: Artificial Sequence
<220> FEATURE:
<223> OTHER INFORMATION: Description of Artificial Sequence:primer 4

<400> SEQUENCE: 4
tgttagactg gaaactttcc a                                            21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:primer 5

<400> SEQUENCE: 5
acggctgtcc aaggagctgc                                              20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:primer 6

<400> SEQUENCE: 6
tgcacctcgc cgcggtactg cacca                                        25

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:primer 7

<400> SEQUENCE: 7
ctcgcggatg gcgctgagg                                               19

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:primer 8

<400> SEQUENCE: 8
gctgcgtaag cggctcctcc gcgatgccg                                    29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:primer 9

<400> SEQUENCE: 9
caccccgtgc tgctgaccga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:primer 10

<400> SEQUENCE: 10
```

```
agggaggcgg ccaccagaag                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:primer 11

<400> SEQUENCE: 11
gccttggggt tcagggggggc                                                    20

<210> SEQ ID NO 12
<211> LENGTH: 22
<212> TYPE: DNA
<213> ORGANISM: Artificial Sequence
<220> FEATURE:
<223> OTHER INFORMATION: Description of Combined DNA/RNA
      Molecule:desoxy-uridine-derivative
<220> FEATURE:
<223> OTHER INFORMATION: Description of Artificial Sequence:primer 12

<400> SEQUENCE: 12
cctgggtcat cttctcgcgg uu                                                  22
```